United States Patent [19]

Halm et al.

[11] Patent Number: 4,966,986

[45] Date of Patent: Oct. 30, 1990

[54] METHOD FOR PREPARING ORGANOHALOSILANES

[75] Inventors: Roland L. Halm, Madison, Ind.; Regie H. Zapp, Carrollton, Ky.

[73] Assignee: Dow Corning Corporation, Midland, Mich.

[21] Appl. No.: 389,135

[22] Filed: Aug. 3, 1989

[51] Int. Cl.$^5$ ............................................... C07F 7/16
[52] U.S. Cl. .................................................... 556/473
[58] Field of Search ......................................... 556/473

[56] References Cited

U.S. PATENT DOCUMENTS 2,488,487 11/1949 Barry et al. ......................... 556/473

FOREIGN PATENT DOCUMENTS 1089726 11/1967 United Kingdom ................. 556/473

Primary Examiner—Paul F. Shaver
Attorney, Agent, or Firm—Robert Spector

[57] ABSTRACT

The present invention provides a method for increasing the yield of methyldichlorosilane obtained from the reaction of silicon metal with methyl chloride without substantially decreasing the combined yield of methyldichlorosilane and dimethyldichlorosilane. This is achieved by blending the methyl chloride with an amount of hydrogen chloride sufficient to accomplish this without forming significant amounts of undesirable $SiCl_4$ and/or $HSiCl_3$. In accordance with a preferred embodiment of the present method the concentration of hydrogen chloride is from 0.1 to about 3 weight percent, based on methyl chloride. Most preferably the hydrogen chloride is present only from the first 50% to about 90% of the methyl chloride addition.

11 Claims, No Drawings

METHOD FOR PREPARING ORGANOHALOSILANES

BACKGROUND OF THE INVENTION

1. Field of the Invention

This invention relates to the preparation of organohalosilanes. More particularly, this invention relates to a method for increasing the yield of monoorganodichlorosilanes using a method referred to in the art as the "direct process" without either adversely affecting the yield of other desirable organochlorosilanes, particularly the combined yield of monoorganodichlorosilane and the corresponding diorganodihalosilanes, or generating substantial quantities of undesirable inorganic halosilanes and organotrihalosilanes.

2. Description of Relevant Art

The preparation of organohalosilanes by the reaction of an alkyl or aryl halide with silicon metal in the presence of various catalysts is known as the "direct process". The halide portion is typically chlorine, but can also be bromine or iodine.

Preparing halosilanes by reacting silicon with hydrogen chloride has been known since the work of Buff and Wohler in 1857 and Combes in 1896. Application of the direct process to the preparation of organohalosilanes was first disclosed by Rochow and his co-workers, beginning in the mid1940's. The art describes numerous improvements to this direct process.

Rochow and Patnode, U.S. Pat. No. 2,380,996, issued Aug. 7, 1945, and Patnode, U.S. Pat. No. 2,380,997, issued Aug. 7, 1945, disclose the preparation of a contact mass for the direct process. The mass is prepared by firing a mixture of silicon, copper, or other metallic catalysts in a reducing atmosphere. Rochow and Patnode and Patnode also disclose the use of nickel, tin, antimony, manganese, silver, and titanium.

Rochow and Gilliam, U.S. Pat. No. 2,383,818, issued Aug. 28, 1945, discloses the use of contact masses comprising silicon and an oxide of copper. Also, included are copper compounds which are readily converted to the oxides, such as copper nitrate.

An example of more recent art is Chapters 4 and 5 of a text entitled Organohalosilanes by R. J. H. Voorhoeve, published in 1967 by Elsevler.

For various reasons, including cost and availability of starting materials, alkylchlorosilanes, particularly methyl- and ethylchlorosilanes, have become the organohalosilanes most frequently prepared by the direct process. The present invention has therefore been limited to this class of alkylchlorosilanes using the corresponding alkyl chlorides. It should be understood that while preferred embodiments of the present invention are directed primarily to the preparation of certain methylchlorosilanes by reacting methyl chloride and silicon, the invention is not to be so limited.

When methyl chloride, represented by the formula MeCl, and silicon metal are reacted using the catalysts and reaction conditions described in the prior art, the resultant products include but are not limited to $MeHSiCl_2$, $Me_2SiCl_2$, $Me_3SiCl$, $MeSiCl_3$, $Me_2HSiCl$, $HSiCl_3$ and $SiCl_4$, where Me represents the methyl radical. By an appropriate selection of catalyst and reaction conditions it is possible to obtain dimethyldichlorosilane, $Me_2SiCl_2$, as the major component, often 90 weight % or more, in the final product mixture. Methyldichlorosilane, $MeHSiCl_2$ typically constitutes about 1 weight percent of the product under these conditions, which are designed to optimize the yield of $Me_2SiCl_2$. The reaction product also typically contains a significant concentration of methyltrichlorosilane, $MeSiCl_3$, which in some instances can be a desired product.

By contrast, the inorganic tetra- and trichlorosilanes, $SiCl_4$ and $HSiCl_3$ are almost always undesirable products of the direct process for preparing methylchlorosilanes. Not only do these inorganic silanes reduce the amount of silicon converted to useful products, but they are difficult to separate from the desired methylchlorosilanes, thereby further increasing the cost of preparing the desired silanes.

If one desires to increase the relative amount of methyldichlorosilane in a direct process product mixture without either a substantial decrease in the combined yield of this product and dimethyldichlorosilane or producing substantial amounts of undesirable products, particularly the inorganic chlorosilanes and, in many instances $MeSiCl_3$, the prior art provides no route for achieving this objective. This art does teach combining the methyl chloride with 5 weight percent or more, based on methyl chloride, of hydrogen chloride as a means for increasing the relative yield of methyldichlorosilane in the final product, however the yield of dimethyldichlorosilane is more than correspondingly reduced and substantial quantities of undesirable inorganic halosilanes are produced. For example, Ariga et al U.S. Pat. No. 3,454,616, which issued on July 8, 1969 teaches reacting silicon metal with mixtures of methyl chloride and from 20 to 83 percent, based on the weight of the mixture, of hydrogen chloride. In accordance with the examples of this patent, when these gaseous mixtures are reacted with metallic silicon containing catalytic amounts of copper and nickel and reaction product contains up to 36 weight percent of methyldichlorosilane. Depending upon reaction conditions and the molar ratio of hydrogen chloride to methyl chloride, the reaction product also contained from 2.4 to 32.5 weight percent of dimethyldichlorosilane, from 5.6 to 33 weight percent of the highly undesirable trichlorosilane and from 0.6 to 2.3 weight percent of $SiCl_4$.

The addition of aluminum chloride or boron trichloride in catalytic amounts to increase the amount of methyldichlorosilane formed by the reaction of methyl chloride and hydrogen chloride with silicon metal is taught in Tamura et al. U.S. Pat. No. 3,109,014, which issued on Oct. 29, 1963. As in the Ariga et al. patent, excessive amounts of the undesirable inorganic halosilanes are produced.

Golubsov et al. report in the Journal of Applied Chemistry, Russian edition, 37 (7), p. 1634 (1964) that the presence of hydrogen chloride increases the yield of phenyltrichlorosilane from the reaction of chlorobenzene and silicon metal. A product containing 55 mole percent of phenyltrichlorosilane and only 0.7 mole percent of phenyldichlorosilane is reportedly obtained from the reaction of a silicon alloy with a mixture of chlorobenzene and hydrogen chloride containing 62 weight percent of hydrogen chloride. The yield of diphenyldichlorosilane is not disclosed.

L. Morozova et al. [Izvestia Akaademii Nauk SSSR Ser. Kim. (1962) (6) 941] reacted a mixture of silicon and catalytic amounts of copper oxide, zinc oxide and sodium silicate with a mixture of methyl chloride and 5 or 10 percent by volume of hydrogen chloride at a temperature of 350° C. Five volume percent of hydrogen chloride produced 43 weight percent of methyldichlorosilane, 2 percent of dimethyldichlorosilane, 31 percent of methyltrichlorosilane, and 6 weight percent of silicon tetrachloride. Ten volume percent of hydrogen chloride yielded 42 weight percent of methyldichlorosilane, 8 percent of methyldichlorosilane and 9 percent of silicon tetrachloride.

The data in an article by Gorbunov et al. in the Sept. 1970 issue of Doklady Akademi Nauk. SSR. 194, 1 (92–94) demonstrate that 35 weight percent of methyldichlorosilane, only about 10 weight percent of dimethyldichlorosilane with about the same amount of silicon tetrachloride is obtained by reacting silicon with a 3:1 weight ratio mixture of methyl chloride and hydrogen chloride at 300 degrees C.

J. Joklik et al. [Collect. Czech. Chem. Commun. (1964) 29(3) 834] disclose reacting silicon with various ratios of methyl chloride to hydrogen chloride in the presence of a copper catalyst at temperatures of 260, 300, and 350° C. At 260° C. as the percent by volume of hydrogen chloride in the hydrogen chloride/methyl chloride mixture was increased from 14 to 40 percent and the weight percent of methyldichlorosilane in the reaction product increased from 8.9 to 14 percent under these conditions the yield of trichlorosilane increased from 4.3 to 15 percent and the yield of $MeSiCl_3$ increased from 25.5 to 32.9%. At 350° C. the yields of methyldichlorosilane, trichlorosilane and silicon tetrachloride were 6.5, 0.4 and 0.3 percent by weight, respectively using 14 volume percent of hydrogen chloride and produced 35.3 weight percent $MeSiCl_3$. When the volume percent of hydrogen chloride was increased to 40 percent the reaction product contained 14.1 weight percent of methyldichlorosilane, 2.9 percent of trichlorosilane and 1.2 percent of silicon tetrachloride.

Finally, the effect of diluting ethyl chloride with various levels of hydrogen chloride was reported on by Andrianov et al. in Izvestiya Akademii Nauk SSSR (Chemical Section) 10, 1788–1794 (1962). Reacting a mixture of 92 weight percent ethyl chloride and 8 percent hydrogen chloride yielded a mixture of chlorosilanes containing 30 percent by weight of trichlorosilane, 12 percent of $SiCl_4$, 8.8 percent of ethyldichlorosilane and 50 percent of diethyldichlorosilane.

SUMMARY OF THE INVENTION

The present invention is based on the discovery that when amounts of hydrogen chloride smaller than reported in the relevant art are blended with at least a portion of the methyl chloride that is reacted with silicon metal to form methylhalosilanes the yield of $MeHSiCl_2$ is increased without substantially decreasing the combined yield of $Me_2SiCl_2$ and $MeHSiCl_2$ or forming significant amounts of the undesirable methyltrichlorosilane or the inorganic chlorosilanes $SiCl_4$ and/or $HSiCl_3$. In accordance with a preferred embodiment, the hydrogen chloride is present only during the first half of the methyl chloride addition.

DETAILED DESCRIPTION OF THE INVENTION

This invention provides an improved method for increasing the yield of methyldichlorosilane produced during the preparation of methylchlorosilanes by the addition of methyl chloride to a reactor containing a reaction mass comprising silicon metal and a suitable catalyst at a temperatures of from 250° to about 350° C. The improvement comprises homogeneously blending at least the initial portion of the methyl chloride with an amount of hydrogen chloride sufficient to increase the yield of methyldichlorosilane without substantially reducing the combined yield of dimethyldichlorosilane and methyldichlorosilane or producing significant amounts of methyltrichlorosilane or inorganic chlorosilanes selected from at least one of trichlorosilane and tetrachlorosilane.

Determination of Optimum Hydrogen Chloride Concentrations

The concentration of hydrogen chloride in the methyl chloride reactant that will increase the yield of methyldichlorosilane without producing significant amounts of inorganic chlorosilanes will depend, at least to some extent, on the conditions under which the methyl chloride and silicon metal are reacted. These conditions include but are not limited to catalyst(s), the presence of reaction promoters, temperature, purity of the reactants, and type of reactor.

The optimum concentration of hydrogen chloride can be determined with a minimum of experimentation by those of ordinary skill in the art of organohalosilane preparation having knowledge of the present invention.

Specifically, using a preferred set of reaction conditions described in the examples that form part of this specification, the present inventors discovered that while the yield of methyldichlorosilane appears proportional to the concentration of hydrogen chloride introduced together with the methyl chloride up to a hydrogen chloride concentration of about 3 weight percent, based on methyl chloride, the combined concentration of undesirable $HSiCl_3$ and tetrachlorosilane does not become significant, i.e. exceed about 2 weight percent of the total reaction product, within this concentration range for hydrogen chloride. In addition, the concentration of $MeSiCl_3$, another undesirable product increases significantly at about 1% HCl. Because of difficulties with product purification and other problems associated with the presence of inorganic chlorosilanes it is preferred to maintain the total amount of these inorganic silanes below about 1 weight percent. This can usually be achieved by using between about 0.01 and about 5 weight % HCl, based on the methyl chloride. This range will vary depending upon reaction conditions and the capacity of the reactor. For particular laboratory scale fluidized bed reactors described in the accompanying examples the upper limit for hydrogen chloride concentration is typically about 1 weight percent.

The present inventors discovered that under the reaction conditions described in the following sections of this specification when the amount of hydrogen chloride introduced into the reactor is from 0.01 to about 1 weight percent, based on methyl chloride (1) the concentration of inorganic halosilanes can be maintained at or below trace amounts (2) the concentration of methyldichlorosilane in the product is substantially increased (3) the combined concentration of dimethyldichlorosilane and methyldichlorosilane in the reaction product is at least 90 weight percent and (4) the concentration of undesirable methyltrichlorosilane is typically below 5%. This concentration range for the hydrogen chloride therefore represents a preferred embodiment of the present method.

When the present method is conducted in a batch or semi-batch mode the present inventors found it desirable to have more of the hydrogen chloride present during the initial methyl chloride addition, and reduce or eliminate hydrogen chloride during the terminal portion of the methyl chloride addition. In accordance with a particularly preferred embodiment hydrogen chloride is present in only the initial 50 to about 90 weight % of the methyl chloride added to the reactor.

Reaction Conditions and Equipment

The optimum concentration range for the hydrogen chloride is at least partially dependent on the type of equipment and reaction conditions used in practicing the present method. Suitable equipment for conducting the direct process include fixed bed, stirred bed and fluid bed reactors. Any of these reactors can be operated in a continuous or batch mode.

It is within the scope of the present invention to utilize the reactor described in U.S. Pat. No. 3,133,109, which issued to Dotson on May 12, 1964 or the one described by Maas et al. in U.S. Pat. No. 4,218,387.

The particle size of the fluidized material should be within the range typically used for the direct process. Dotson in U.S. Pat. No. 3,133,109 discloses particle size range of from 20 to 200 microns. Depending upon the capacity of the reactor, a range of from 1 to 200 microns is preferred for the present method.

The temperature range used for the direct process is typically from 250° to about 350° C. Temperatures within the range of from 260° to about 330° C. are preferred to optimize yields of the desired methylchlorosilanes.

The art pertaining to the direct process for preparing alkylhalosilanes discloses a variety of catalysts and promoters suitable for use in the direct process. U.S. Pat. No. 4,500,724, which issued to Ward et al. discloses catalysts for the production of organohalosilanes comprising copper and copper oxides, tin or tin-containing compounds, and zinc or zinc-containing compounds. Halm et al. in U.S. Pat. No. 4,602,101, issued July 22, 1986, discloses a method for controlling a process for the manufacture of alkylhalosilanes, said process comprising contacting an alkyl halide with metallurgical grade silicon, at a temperature of 250°-350° C., in the presence of tin or tin compounds, and copper or copper compounds, wherein there is present as a promoter phosphorus or phosphorous-containing compounds.

Other suitable catalysts and promoters include but are not limited to calcium, barium, titanium, zirconium, cadmium, lead, bismuth, arsenic, nickel, antimony, silver, brass, cobalt, iron, carbon, and aluminum. Any of these promoters can be used in their elemental form or as compounds that contain the element and are capable of liberating the element under the reaction conditions of the direct process.

Preferred catalyst/promoter compositions include but are not limited to:
1. (a) Copper or a copper compound and (b) zinc or a zinc compound;
2. (a) Copper or a copper compound, (b) zinc or a zinc compound and (c) tin or a tin compound;
3. (a) Copper or a copper compound, (b) tin or a tin compound, and (c) optionally arsenic or an arsenic compound;
4. (a) Copper in the form of a mixture, alloy or compound, (b) at least one member selected from the group consisting of tin, tin compounds, zinc and zinc compounds, and (c) at least one of phosphorus, phosphorus compounds, phosphorus-containing alloys, and metal phosphides;
5. (a) Copper or a copper compound, (b) tin or a tin compound, (c) arsenic or an arsenic compound, and (d) phosphorus or a phosphorus compound;
6. (a) Iron alloyed with silicon or a mixture of iron and aluminum alloyed with silicon, (b) copper or at least one copper compound, optionally at least one of the following (c) tin and tin compounds, (d) phosphorus in the form of elemental phosphorus, at least one metal phosphide, or a phosphorus-containing alloy, and (e) zinc or a zinc compound; and
7. (a) A mixture of copper and zinc that is present as brass, (b) cuprous chloride (c) tin and tin compounds and (d) a metal phosphorus alloy.

The metal portion of the metal phosphorus alloy or phosphide is preferably aluminum, calcium, copper, or zinc.

The present catalysts and promoters are typically used in amounts as low as several parts per million. Up to 10 weight percent, based on initial silicon, of some of the aforementioned catalysts have been used.

For best results, the purity of the silicon should be at least 95% but less than 100%. A metallurgical grade of silicon is preferred. For optimum results the silicon is in a particulate form.

The following examples describe preferred embodiments of the present invention with respect to types and concentrations of reactants, catalysts, promoters, process conditions and equipment, and should not be interpreted as limiting the present invention as defined in the accompanying claims. Unless otherwise indicated all parts and percentages in the example are by weight, all quantities expressed in parts per million are based on the weight of all materials initially charged to the reactor together with the silicon, and all prior art mentioned is incorporated by reference thereto.

The reactions between silicon and methyl chloride was conducted in a fluidized bed reactor of the type described in U.S. Pat. No. 3,133,109 to Dotson. The temperature of the sand bath was 315° C. and each heating period, equivalent to the reaction time, was 44 hours in duration.

Metallurgical grade silicon (Globe Metallurgical, Inc. Beverly, Ohio) was employed which contained aluminum (0.22%), calcium (0.046%), and iron (0.34%). The hydrogen chloride used was of 99.999% minimum purity, obtained from Matheson Gas Products, Dayton, Ohio. The methyl chloride and hydrogen chloride were individually metered using calibrated flowmeters. When hydrogen chloride was used the two gas streams were combined and passed through a static mixer to ensure proper blending prior to being introduced into the reactor.

The material used as the reaction mass was prepared by blending the following ingredients to homogeneity in a suitable container: 100 parts of silicon, 6.48 parts of cuprous chloride, 600 parts per million (ppm) brass (a 1/1 weight ratio alloy of copper and zinc), 30 ppm tin and 2000 ppm copper phosphorus alloy containing 13.5 weight percent phosphorus. The resultant mixture of ingredients was mixed shaking vigorously for 2 to 3 minutes. This mixture was then charged to the reactor, following which the reactor was closed and placed in the 315° C. sand bath. At this time a stream of nitrogen was passed through the reactor. The sand bath was continuously fluidized to maintain a constant temperature within the reactor.

When the temperature of the reactor reached about 315° C. the nitrogen was replaced with a stream of gaseous methyl chloride as the fluidizing medium. The flow of methyl chloride was continued for 44 hours. When hydrogen chloride was added it was blended with the methyl chloride throughout the entire methyl chloride addition or only for the first 28 hours, at which time the hydrogen chloride addition was discontinued.

The products emerging from the reactor were condensed and collected in previously weighed cold traps immersed in a bath of dry ice and isopropanol. The liquid collected in the tubes was then transferred to bottles cooled with dry ice/isopropanol and then injected into the sample chamber of a gas chromatograph using a previously cooled syringe. The chromatograph was used to determine the types and concentration of reaction products.

EXAMPLE 1

(Control Example)

This example typifies the product distribution obtained in the absence of hydrogen chloride.

The product distributions from two runs performed without the addition of hydrogen chloride were determined and the results were averaged. The averaged values, reported here and summarized in Table 1, were:
92.1% $Me_2SiCl_2$
1.4% $MeHSiCl_2$
4.1% $MeSiCl_3$ The remaining material was a mixture of other methylchlorosilanes. There were no detectable amounts of $HSiCl_3$ or $SiCl_4$ present.

EXAMPLE 2

This example demonstrates the advantages of blending from 0.2 to 2 weight percent hydrogen chloride with the methyl chloride reactant. The reaction described in example 1 was repeated with the exception that the amounts of hydrogen chloride listed in Table 1 were blended with the methyl chloride throughout the entire methyl chloride addition. The reaction products contained the indicated amounts of $HSiCl_3$ and/or $SiCl_4$. The quantity of HCl employed and the percentage of the principal products are shown in the following table, based on an average of two runs.

TABLE 1

| HCl added (Wt %) | Products (Weight % of Total) | | | | |
|---|---|---|---|---|---|
| | $Me_2SiCl_2$ | $MeHSiCl_2$ | $MeSiCl_3$ | $HSiCl_3$ | $SiCl_4$ |
| 0.0 | 92.1 | 1.3 | 4.1 | 0.00 | 0.00 |
| 0.2 | 90.4 | 2.1 | 4.4 | 0.00 | 0.00 |
| 0.4 | 89.4 | 3.3 | 5.0 | 0.05 | 0.02 |
| 0.72 | 89.1 | 3.5 | 5.2 | 0.01 | 0.00 |
| 0.85 | 84.5 | 5.6 | 7.1 | 0.34 | 0.00 |
| 1.00 | 75.0 | 8.9 | 11.8 | 1.46 | 0.50 |
| 1.5 | 73.1 | 9.5 | 10.7 | 3.44 | 0.56 |
| 1.5 | 74.6 | 9.2 | 11.3 | 1.63 | 0.37 |
| 2.0 | 79.5 | 7.0 | 9.5 | 1.11 | 0.23 |

Weight percent HCl is based on methyl chloride

The remaining material in the reaction product was a mixture of other methylchlorosilanes.

The data reported in Table 1 demonstrate that at a hydrogen chloride concentration of 0.85 weight percent the amount of $MeHSiCl_2$ more than quadrupled from the value reported in example 1 with only a small reduction in the combined yield of $Me_2SiCl_2$ and $MeHSiCl_2$, and only trace amounts of $HSiCl_3$ and $SiCl_4$. When the hydrogen chloride concentration was increased to 1.0% the yield of both $MeHSiCl_2$ and the undesirable $HSiCl_3$ and $SiCl_4$ increased significantly.

EXAMPLE 3

This example demonstrates the advantage with respect to yield of $MeHSiCl_2$ obtained adding hydrogen chloride during only the first portion of the methyl chloride addition. The procedure described in example 2 was repeated, with the exception that 1 weight percent of hydrogen chloride was blended with the methyl chloride only during the first 28 hours of the methyl chloride addition, at which time the addition of hydrogen chloride was discontinued.

The product was collected throughout the reaction and exhibited the following composition, expressed as percent by weight of the total product mixture:

| $Me_2SiCl_2$ | $MeHSiCl_2$ | $MeSiCl_3$ | $HSiCl_3$ | $SiCl_4$ |
|---|---|---|---|---|
| 87.7 | 4.7 | 5.16 | 0.17 | 0.00 |

As in the previous examples, the remaining yield was a mixture of methylchlorosilanes.

Although the total amount of hydrogen chloride added was 0.64 weight percent, based on total methyl chloride, the 4.71 weight percent yield of $MeHSiCl_2$ is higher than the value of 3.54 percent obtained when 0.72 weight percent of hydrogen chloride was added during the entire methyl chloride addition with no reduction in the combined yield of methyldichlorosilane and dimethyldichlorosilane and only trace amounts of the undesirable inorganic chlorosilanes.

What is claimed is:

1. In a method for increasing the yield of methyldichlorosilane produced during the preparation of methylchlorosilanes by the addition of methyl chloride to a reactor containing a reaction mass comprising silicon metal and a suitable catalyst at a temperature of from 250 to about 350° C., the improvement comprising homogeneously blending at least the initial portion of the methyl chloride with an amount of hydrogen chloride sufficient to increase the yield of methyldichlorosilane without substantially reducing the combined yield of dimethyldichlorosilane and methyldichlorosilane, producing more than 5 weight percent of methyltrichlorosilane or producing more than trace amounts of inorganic chlorosilanes selected from at least one of trichlorosilane and tetrachlorosilane.

2. A method according to claim 1 wherein the amount of hydrogen chloride added is from about 0.01 to about 5 weight percent, based on the weight of the methyl chloride, the reaction between the methyl chloride and silicon is conducted at a temperature of from 260° to about 330° C. in the presence of said catalyst and at least one reaction promoter.

3. A method according to claim 2 where hydrogen chloride is added during the entire reaction.

4. A method according to claim 2 where the reaction is conducted in a batch or semi-batch type reactor and hydrogen chloride is added during the initial 50 to 90% of the methyl chloride addition.

5. A method according to claim 2 wherein the total amount of hydrogen chloride added is equal to between about 0.01 and about 2% based on the weight of the methyl chloride, the combined concentration of inorganic chlorosilanes in the product mixture does not exceed 2 weight percent.

6. A method according to claim 5 where the reaction mass comprises (a) metallurgical grade silicon, (b) a catalytically effective amount of copper or a copper compound in combination with at least one member selected from the group consisting of zinc and zinc compounds, tin and tin compounds and a reaction promoter selected from the group consisting of elemental phosphorus, phosphorus-containing alloys and metal phosphides.

7. A method according to claim 6 where said reaction mass also includes iron alloyed with silicon or a mixture of iron and aluminum alloyed with silicon.

8. A method according to claim 6 where the metal portion of said metal phosphide is aluminum, calcium, copper, tin or zinc.

9. A method according to claim 8 where the reaction mass additionally contains at least one member selected from the group consisting of arsenic and arsenic compounds.

10. A method according to claim 6 where copper and zinc are present as brass, the copper and phosphorus are present as cuprous chloride and a copper phosphorus alloy, and the reaction mass includes tin or a tin compound.

11. A method according to claim 6 where said reaction mass comprises silicon and a catalytically effective amount of copper or a copper compound, tin or a tin compound, arsenic or an arsenic compound and phosphorus or a phosphorus compound.

* * * * *